United States Patent [19]
Fox

[11] Patent Number: 6,156,057
[45] Date of Patent: Dec. 5, 2000

[54] METHOD FOR INDUCING HYPOTHERMIA

[76] Inventor: James Allan Fox, 3708 Carlson Cir., Palo Alto, Calif. 94306

[21] Appl. No.: 09/442,162

[22] Filed: Nov. 16, 1999

Related U.S. Application Data

[63] Continuation of application No. 08/909,752, Aug. 12, 1995, Pat. No. 6,090,132.
[60] Provisional application No. 60/024,218, Aug. 15, 1996.
[51] Int. Cl.[7] .................................. A61F 7/00; A61F 7/12
[52] U.S. Cl. .............................. 607/96; 607/99; 607/109; 607/115; 607/116; 607/135
[58] Field of Search ..................... 607/96, 104, 108–112, 607/114, 115–116, 136; 165/46

[56] References Cited

U.S. PATENT DOCUMENTS

| | | | |
|---|---|---|---|
| 4,425,917 | 1/1984 | Kuznetz | 607/110 |
| 4,750,493 | 6/1988 | Brader . | |
| 4,781,193 | 11/1988 | Padgen | 607/110 X |

(List continued on next page.)

OTHER PUBLICATIONS

Boulant, Jack A., Thermoregulation In: *Fever, Basic Mechanisms, and Management* Edited by Mackowieck pp. 1–21 Raven Press, New York (1991).

Busto, R., et al., "Small Differences in Intraischemic Brain Temperature Critically Determine the Extent of Ischemic Neuronal Injury", *J. of Cerebral Blood Flow and Metabolism* 7:729–738 (1987).

Cheng et al., "Increasing Mean Skin Temperature Linearly Reduces the Core–Temperature Thresholds for Vasoconstruction and Shivering in Humans," *Anesthesiology* 82:1160–1168 (1995).

Colbourne et al., "Delayed Postischemic Hypothermia: A Six Month Survival Study Using Behavioral and Histological Assessment of Neuroprotection," *The Journal of Neuroscience* 15(11):7250–7260 (1995).

Marion et al., "Resuscitative Hypothermia," *Critical Care Med.* 24(2):S81–S89 91996).

Meden et al., "The Influence of Body Temperature on Infarct Volume and Thrombolytic Therapy in a Rat Embolic Stroke Model," *Brain Research* 647:131–138 (1994).

Morikaw et al., "Effect of Moderate Intraischemic Hypothermia of Brain Focal Injury Following Reversible Middle Cerebral Artery Occlusion," *J. Cerebral Blood Flow and Metabolism* II: Suppl. 2 S116 Raven Press, N.Y. (1991).

Sessler, Daniel. I., "Deliberate Mild Hypothermia," *Journal of Neursurgical Anesthesiology* 7(1):38–46 (1995).

Sternau et al., "Intracranial Temperature–Observations in the Human Brain," *J. Cerebral Blood Flow and Metabolism* II: Suppl. 2 S123 Raven Press, N.Y. (1991).

Xue et al., "Immediate or Delayed Mild Hypothermia Prevents Focal Cerebral Infarction," *Brain Research* 587:66–72 (1992).

*Primary Examiner*—Cary O'Connor
*Assistant Examiner*—Ryan Carter
*Attorney, Agent, or Firm*—Robins & Associates

[57] ABSTRACT

The invention relates generally to methods and apparatus for inducing hypothermia in an animal. Known methods for inducing hypothermia all involve cooling the outside or inside of an animal, sometimes in conjuction with drugs that disable the animal's homeostatic responses. The present invention is directed to a method and apparatus for applying heat to the hypothalamus of a warm-blooded animal in order to utilize the physiological mechanisms that regulate body temperature to effect a compensatory cooling response, thereby lowering body temperature. It is new and unsuggested in the art to apply heat in an effort to reduce body temperature. The invention effects the desired lowering of body temperature by the method of raising the temperature of the hypothalamus, a brain structure situated in humans just above the pituitary gland responsible for temperature regulation, by warming a nasal passage, or a sinus, such as the sphenoid sinus that is nearest to the hypothalamus, or by direct warming of the hypothalamus, or a combination of these.

11 Claims, 5 Drawing Sheets

U.S. PATENT DOCUMENTS

| | | |
|---|---|---|
| 4,920,963 | 5/1990 | Brader . |
| 5,383,854 | 1/1995 | Safar et al. . |
| 5,464,834 | 11/1995 | Peglion . |
| 5,471,767 | 12/1995 | Walker . |
| 5,474,533 | 12/1995 | Ward . |
| 5,486,204 | 1/1996 | Clifton . |
| 5,782,798 | 7/1998 | Rise . |

METHOD FOR INDUCING HYPOTHERMIA

CROSS-REFERENCE TO RELATED APPLICATION

This application is a continuation of application Ser. No. 08/909,752, filed Aug. 12, 1997, now U.S. Pat. No. 6,090,132, from which priority is claimed pursuant to 35 U.S.C.§120 and which is incorporated herein by reference in its entirety. This application is further related to provisional patent application ser. No: 60/024,218, filed Aug. 15, 1996, and which is incorporated herein by reference in its entirety.

TECHNICAL FIELD

The invention relates generally to methods and apparatus for inducing hypothermia in an animal, and more particularly relates to methods and apparatus for warming a nasal passage, or a sinus, or the hypothalamus, or a combination of these, of an animal. The invention additionally relates to methods and apparatus for applying compounds to the nasal tissues of an animal in order to induce hypothermia.

BACKGROUND

More than half-a-million Americans suffer strokes every year, and a similar number suffer head trauma each year. Some of these people die of their injuries; however, most survive with some degree of neurological damage. Although many treatments and therapies have been attempted, none are very effective in reducing neurological damage following stroke, head trauma, or other such condition. One of the most effective therapies known for these and similar conditions is hypothermia, the lowering of body temperature. Even small reductions in body temperature after the initial injury has occurred can reduce damage and improve neurological outcome, if treatment is not delayed too long after the incident. In fact, hypothermia has been a confounding variable in animal experiments directed at discovering pharmacological compounds which may reduce neurological damage following experimentally-induced trauma; some compounds thought to be directly neuroprotective have instead been found to lower body temperature in the small-bodied experimental animals used in studies. When the body temperature of these animals is artificially maintained at the normal level during drug treatment, some of these promising drugs have been found not to be neuroprotective, revealing that the effective treatment was hypothermia, and not the drug. Accordingly, it is desireable to discover a method for inducing hypothermia in humans.

Body temperature is very well regulated in warm-blooded animals. However, the pharmacological compounds that may lower the body temperature of a mongolian gerbil or a rat (with large body surface areas compared to their small volumes) do not effectively produce hypothermia in larger animals such as humans. It is very difficult to cool humans due to our larger mass, smaller surface area in proportion to our volume, and our complex homeostatic mechanisms geared towards maintaining our body temperature.

However, although difficult, it is possible to cool large animals and humans. Hypothermia (the condition of lower-than-normal body temperature in a warm-blooded animal) has been investigated in animals for many years, and has been used on human patients (for example, in heart surgery) for more than forty years. It is known to reduce neurological damage otherwise resulting from cardiac arrest., stroke and trauma. Known methods for inducing hypothermia all involve cooling the outside or inside of an animal, sometimes in conjuction with drugs that disable the animal's homeostatic responses. Present methods for inducing hypothermia include externally applied cold packs, ice blankets, infusion of cold saline into arteries and into the peritoneum of an animal, blowing air across an animal's skin, wetting the skin or hair of an animal, and cooling the air around an animal. One method, preferred by some researchers, includes infusion of saline into the peritoneum of an animal in order to cool a large volume of blood and tissue in contact with the peritoneum. However, this is no simple procedure, but is an invasive procedure that requires puncture of the abdominal wall, infusion of cool or cold saline, and monitoring of fluid and electrolyte balance of the animal for the duration (and beyond) of the procedure. Hypothermia may also be a side-effect of general anesthesia during surgery.

However, these methods are impractical because they require trained personnel and dedicated equipment, and often induce discomfort in the animal or are invasive. In many of the above examples, careful co-ordination and oversight by medical personnel is required since drastic measures need be taken to overcome the normal operation of the animal's physiological responses to cold. These responses include vasoconstriction, shunting of blood away from the limbs and retention of blood in the body core (away from cold blankets, wet skin, etc.) and shivering. Suppression of these responses by muscle relaxants, vasodilators and other drugs may also cause, as side-effects, suppression of other vital body functions associated with breathing, maintenance of-blood pressure, heart rate, and other vital bodily functions. These side-effects, such as circulatory shock, may be serious. They increase risk and limit the effectiveness of hypothermia treatments in humans. Thus, there is at present no simple, effective method for inducing and maintaining hypothermia in an animal.

All of the above-mentioned methods for inducing hypothermia, with the possible exception of some potent centrally-active drug regimens that disable thermoregulation, must work to oppose the animal's bodily efforts to maintain body temperature. Difficulties with these techniques arise because the homeostatic mechanisms and physiological responses involved in regulation of body temperature are among the most basic responses in warm-blooded animals. Cooling by cold blankets and dressings is uncomfortable, induces shivering which must be opposed by medication, and causes vasoconstriction which reduces pa blood flow to the cooled extremities, reducing the effectiveness of the cooling treatment. Cooling by intra-arterial infusion of cold blood or saline is invasive, of limited utility because of limited ability to deliver large volumes of cooled fluid, requires medical equipment and supervision, and may potentially cause vascular, cardiac and neurological (if emoboli are created) side-effects. Pharmaceutical treatments that disable thermoregulatory responses often have other effects as well, and require active cooling measures such as those already mentioned in order to lower body temperature of a large animal. Thus, an ideal method for inducing hypothermia in a warm-blooded animal would not require drastic invasive measures or drugs, and would not oppose the animal's physiological temperature control mechanisms, but would make use of them to achieve hypothermia.

OVERVIEW OF RELATED ART

The following references relate to one or more aspects of the present invention:

U.S. Pat. No. 4,750,493 to Brader is directed to a method for cooling the extracranial area including the face during emergency care of cardiac arrest of severe shock in order to induce vasoconstriction and intracranial hypothermia. This invention is implemented by a topical cold pack described in the patent. This method of cooling does not directly cool the hypothalamus, nor would it trigger a physiological cooling response if it did. Instead, the physiological response of the hypothalamus to such extracranial cooling would be to oppose body cooling.

U.S. Pat. No. 4,920,963 to Brader is also directed to a method and apparatus for cooling the extracranial area including the face during emergency care of cardiac arrest of severe shock, and discloses an apparatus which includes a watertight shroud for the head. Again, this patent would not directly cool the hypothalamus, and if it did, would tend to elicit a physiological response that would act to oppose body cooling.

U.S. Pat. No. 5,383,854 to Safar, Strezoski and Klain is directed to a cardiopulmonary bypass apparatus adaptable to include a module that includes a heat exchanger capable of cooling the blood.

U.S. Pat. No. 5,464,834 to Peglion, Goument, Millan and Rivet is directed to chemical compounds acting at a $5-HT_{1A}$ receptor capable of inducing hypothermia in rats.

U.S. Pat. No. 5,474,533 to Ward, Brown and Dzwonczyk is directed to a method and apparatus for treating patients suffering from cardiac arrest, shock, respiratory failure, hypothermia, hyperthermia, and head injury, capable of modulating a patient's body temperature.

U.S. Pat. No. 5,486,204 to Clifton is directed to a method for treating severe brain trauma with hypothermia. Hypothermia in human patients was induced by wrapping patients in cooling blankets, and administering drugs such as muscle relaxants and sedatives.

SUMMARY OF THE INVENTION

Known methods for inducing hypothermia all involve cooling the outside or inside of an animal, sometimes in conjuction with drugs that disable the animal's homeostatic responses. It is new and unsuggested in the art to apply heat in an effort to reduce body temperature. The present invention is directed to a method and apparatus for applying heat to the hypothalamus of a warm-blooded animal in order to utilize the physiological mechanisms that regulate body temperature to effect a compensatory cooling response, thereby lowering body temperature. The present invention takes advantage of physiological temperature-regulatory mechanisms and makes direct use of their action, instead of striving to oppose or disable them.

It is well-known that the main brain center for regulation of body temperature is in the hypothalamus, a brain structure situated in humans just above the pituitary gland. Decreasing the temperature of the hypothalamus, as occurs when core body temperature is reduced, triggers compensatory responses to cold, such as vasoconstriction and shivering. Conversely, warming the hypothalamus triggers compensatory responses that cool the animal, such as vasodilation and sweating. Thermoregulatory responses can be quite effective, as humans routinely live and work in environments where the external temperature is higher or much lower than normal body temperature.

The hypothalamus is very sensitive to small changes in body temperature. A temperature change of 0.2 degrees Celsius (° C.) is sufficient to trigger sweating in a human subject. Sweating is a major mechanism for cooling in humans. Sweating will continue as long as the hypothalamic temperature is above its setpoint for temperature control.

Thus, for example, if the temperature of the hypothalamus in a human patient is raised to about 0.2° C. or more above its setpoint, the patient will respond with such physiological cooling responses as vasodilation and sweating. These responses may continue indefinitely in response to sustained raised temperature of the hypothalamus. These physiological cooling responses will act to lower the body temperature of the patient.

In humans, the hypothalamus is located near to the sphenoid sinus, one of the sinuses accessible through the nose or mouth. Heat may be applied via the sinuses, or more particularly to the sphenoid sinus, in order to warm the hypothalamus and so to trigger a cooling response. Alternatively, heat may be applied directly to the hypothalamus. Heating of the hypothalamus may be accomplished with little heating of surrounding brain regions. Heat applied near the surface of the skull will penetrate a small distance, but blood flow and other thermal effects will cause the heating to be localized to the portion of the brain nearest the application of the heat. Thus, mild local heating of the sphenoid sinus or other nasal passages or sinuses in order to warm the bypothalamus would not cause undue heating of other portions of the brain. Alternatively, warming the nasal passages themselves can trigger sweating and so be effective for lowering body temperature.

Accordingly, a primary object of the present invention is to provide a method for inducing hypothermia which does not require cooling measures such as application of cold packs, cold blankets, infusion of cold saline, does not require drastic invasive measures or drugs, and would not oppose an animal's physiological temperature control mechanisms, but would instead make use of them to achieve hypothermia.

It is a further object of the invention to provide a method of inducing hypothermia by applying heat to a nasal passage.

It is a further object of the invention to provide a method of inducing hypothermia by applying heat to a sinus of an animal. In particular, it is an object of the present invention to provide a method of inducing hypothermia in a person by applying heat to a sphenoid sinus.

It is a further object of the invention to provide a method of inducing hypothermia by warming the hypothalamus of an animal.

It is another object of the invention to provide an apparatus for warming a nasal passage of an animal.

It is another object of the invention to provide an apparatus for warming a sinus of an animal.

It is a further object of the invention to provide an apparatus for warming a sphenoid sinus.

It is another object of the invention to provide an apparatus for warming the hypothalamus of an animal.

It is another object of the invention to provide an apparatus for introducing compounds into a nasal passage of an animal.

It is a further object of the invention to introduce compounds into a sinus of an animal.

Additional objects, advantages and novel features of the invention will be set forth in part in the description which follows, and in part will become apparent to those skilled in the art upon examination of the following, or may be learned by practice of the invention.

In one aspect, the invention is a method for inducing hypothermia which comprises providing a heat-generating means and, with this heat generating means, applying heat to a nasal passage, or a nasal passage and a sinus, or a nasal passage, sinus and hypothalamus, or to a sinus and hypothalamus, or to the hypothalamus. This application of heat to a nasal passage, or a nasal passage and sinus, or sinus and hypothalamus, or hypothalamus will result in a physiological response effective to lower the body temperature of the animal so treated.

In another aspect, this invention is an apparatus for applying heat to a nasal passage, or a nasal passage and a sinus, or a nasal passage, sinus and hypothalamus, or to a sinus and hypothalamus, or to the hypothalamus. Application of heat through the use of said apparatus to a nasal passage, or a nasal passage and a sinus, or a sinus and the hypothalamus, or the hypothalamus will result in a physiological response effective to lower the body temperature of the animal so treated.

DETAILED DESCRIPTION OF THE INVENTION

Definitions.

Before the present methods and apparatus are disclosed and described, it is to be understood that this invention is not limited to specific methods, means and apparatus, as methods for applying heat, means for directing the heat so applied, and apparatus for applying heat to a nasal passage, sinus, brain region or anatomical structure may, of course, vary. It is also to be understood that the terminology used herein is for the purpose of describing particular embodiments only and is not intended to be limiting.

It must be noted that, as used in the specification and the appended claims, the singular forms "a", "an", and "the" include plural referents unless the context clearly states otherwise. Thus, for example, reference to "a sinus" includes more than one sinus.

The term "animal" is meant to include humans and other warm-blooded animals.

By the term "hypothermia" is meant the condition of lower-than-normal body temperature in a warm-blooded animal, that is, a reduction in, or lowering of, body temperature in an animal.

The term "heat" is used in its conventional sense to mean thermal energy content or warmth; the verb-form of the term, "to heat", is used herein to mean to transfer thermal energy, to increase the temperature of, to warm.

The term "hypothalamus" as used herein is meant to include the anatomical region of the brain termed in standard neuroanatomical usage the hypothalamus, but is not meant to be strictly limited to this neuroanatomical region. As used herein, the term "hypothalamus" is meant to include the brain regions generally accepted as being important in the regulation of body temperature in warm-blooded animals, particularly the pre-optic and suprachiasmatic nuclei of the hypothalamus, including neighboring areas of the brain such as the septum that have been found to be important in thermoregulation.

The terms "nasal passage" and "nasal passages" are used herein to include the nostrils and to mean the anatomical regions connecting the nostrils with the sinuses of the skull.

The term "oral passage" is meant herein to include the mouth and throat, and the opening connecting the oral cavity with the nasal passages behind the palate.

By the term "physiological cooling response" is meant the physiological and behavioral responses of an animal to warming, or to stimuli that usually accompany warming, usually effective to cool the animal. Responses that are usually effective to cool an animal are effective to rid the animal of excesss heat or to reduce the body temperature of the animal, and may include, but are not limited to sweating, peripheral vasodilatation, panting, drooling, licking, and repositioning the body.

DETAILED DESCRIPTION OF A PREFERRED EMBODIMENTS OF THE INVENTION

Method of Use

Figure 1:
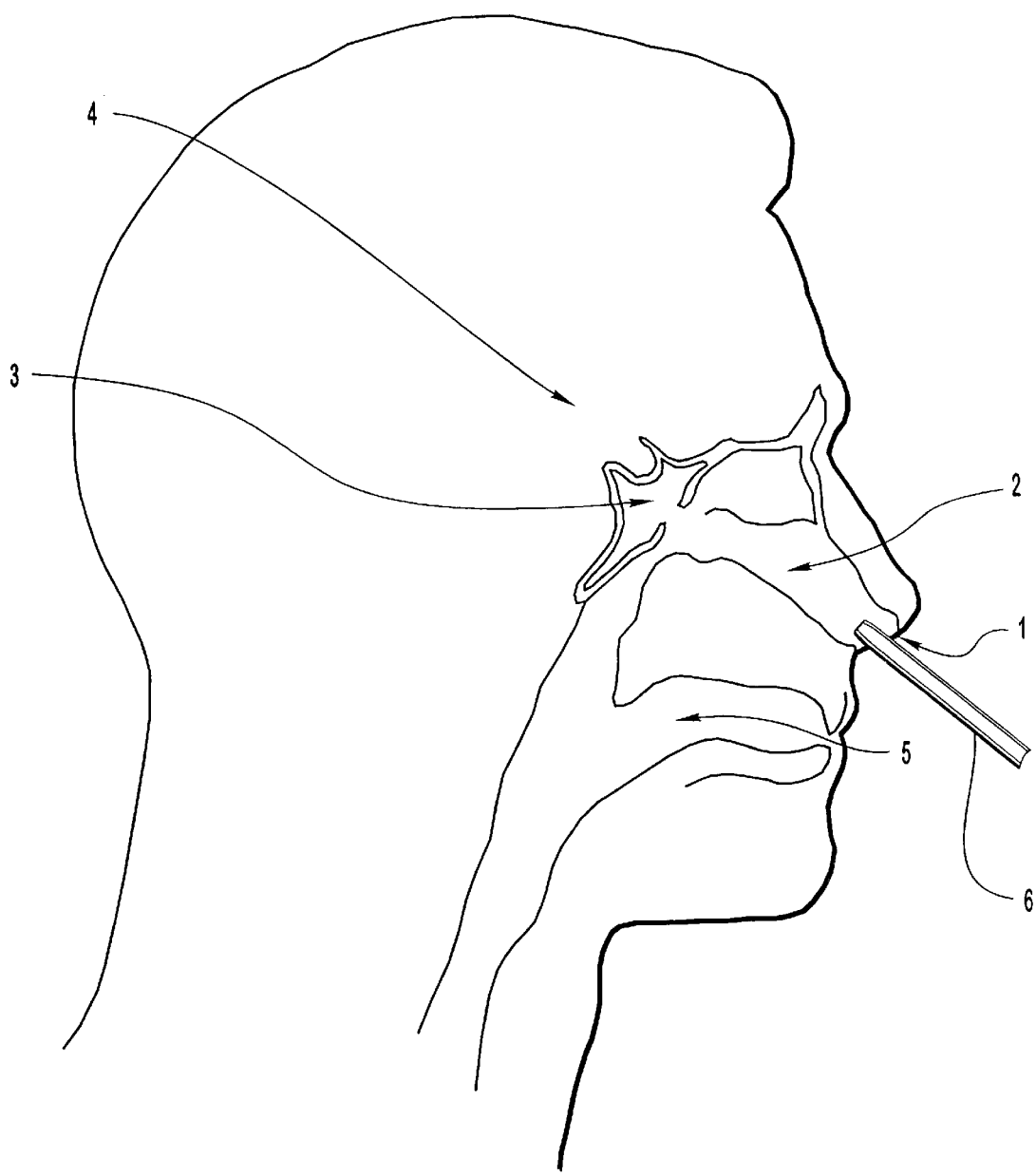
FIG. 1 is a cross-sectional view of a human head, showing placement of a tube in a nostril.
Figure 2:
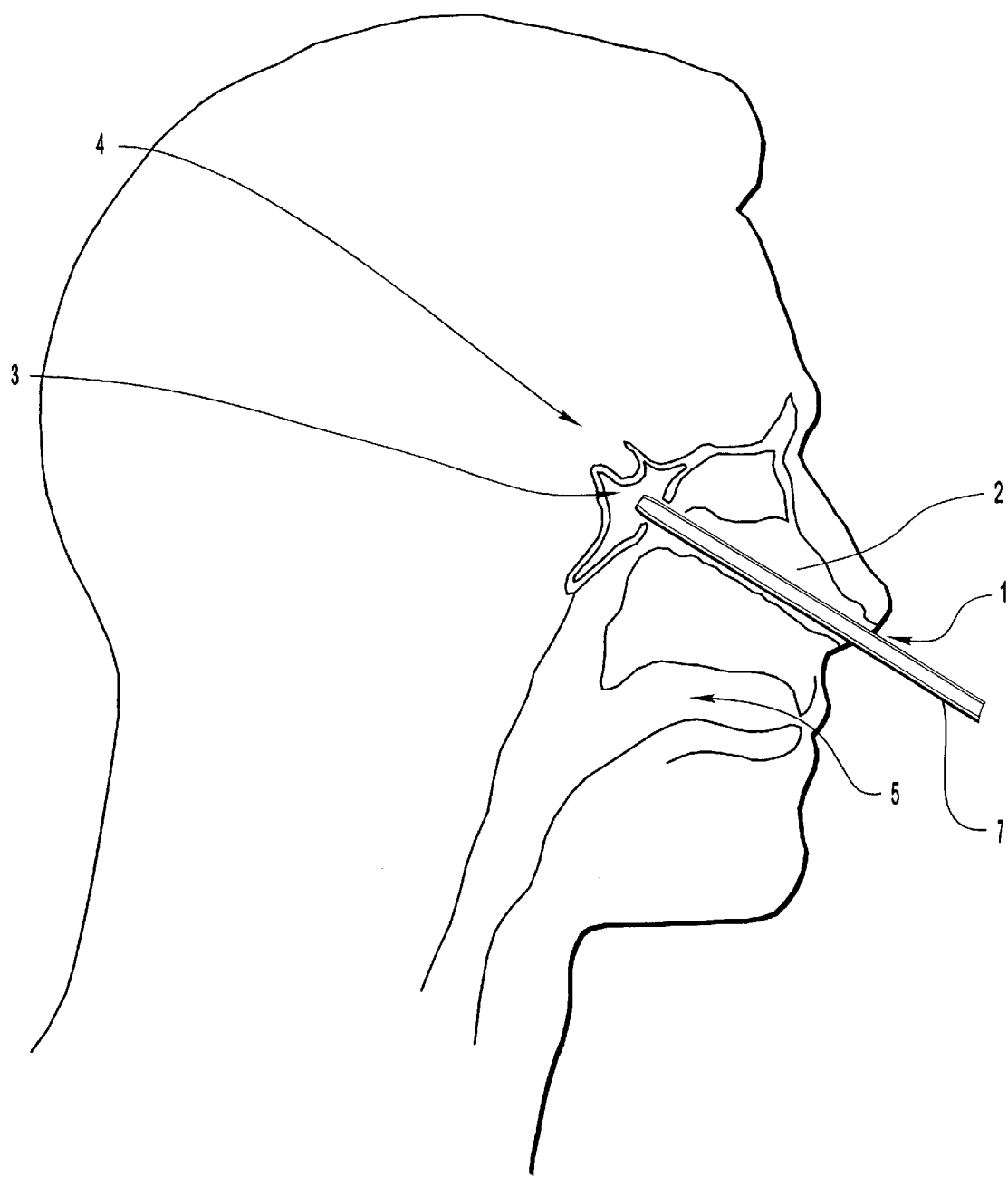
FIG. 2 is a cross-sectional view of a human head, showing placement of a warming device into the sphenoid sinus.
Figure 3:
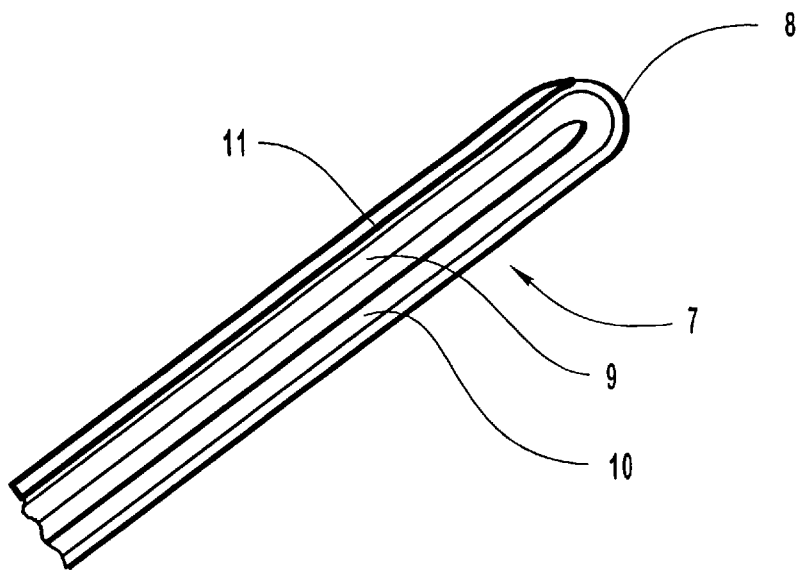
FIG. 3 is a cross-sectional view of a dual-lumen catheter with an occluded end.
Figure 4:
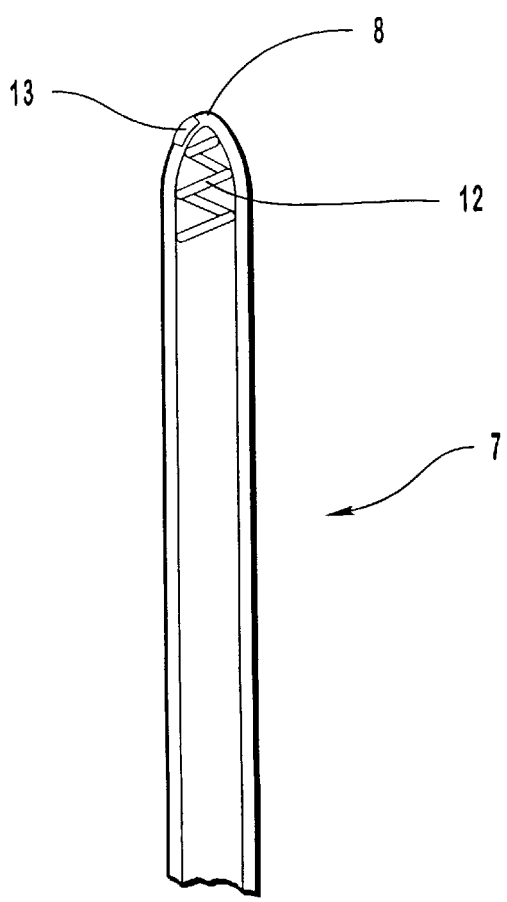
FIG. 4 is a cross-sectional view of an electrically-heated device with a thermal sensor.
Figure 5:
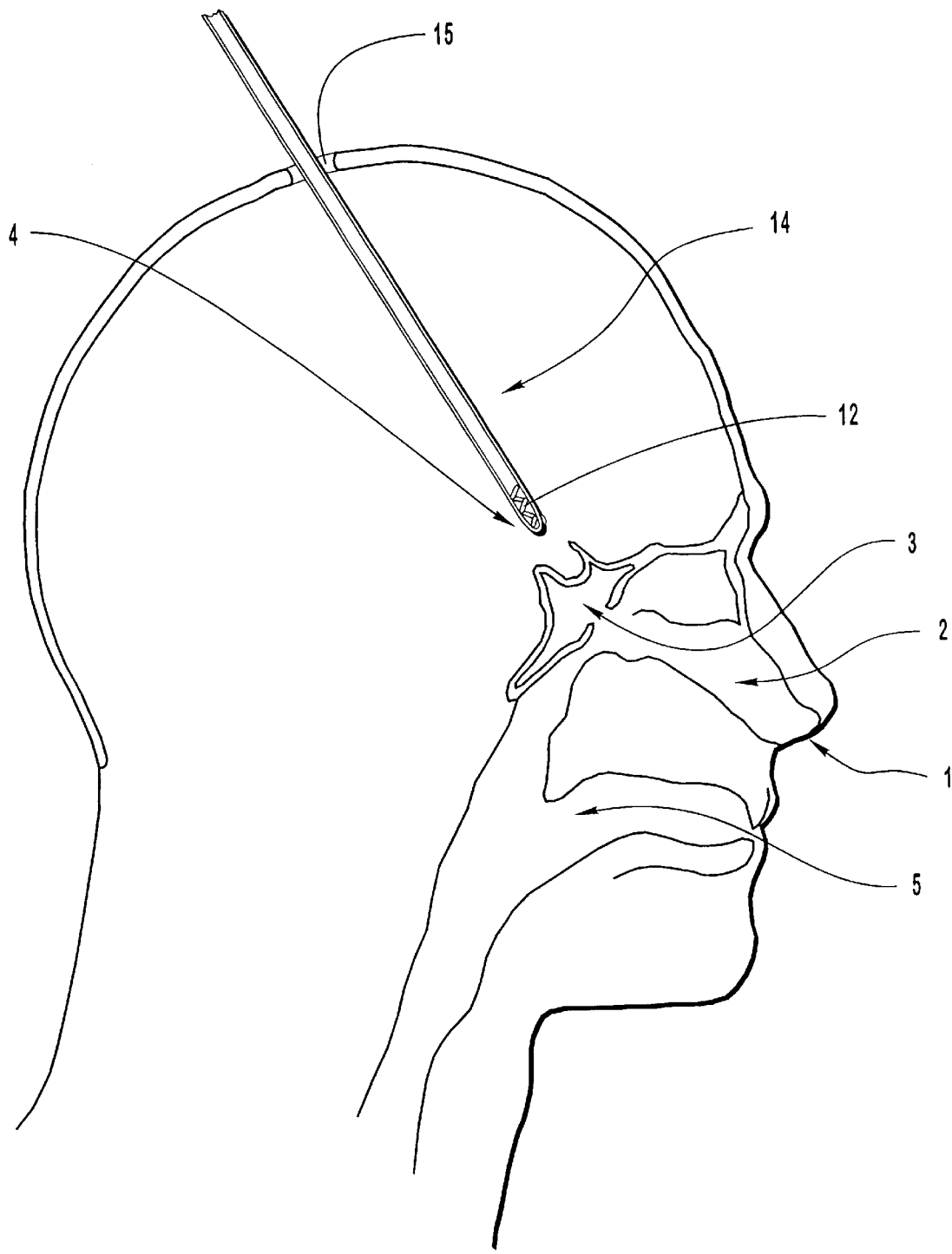
FIG. 5 is a cross-sectional view of a human head, showing placement of heating means into the hypothalamic region of the brain.
Figure 6:
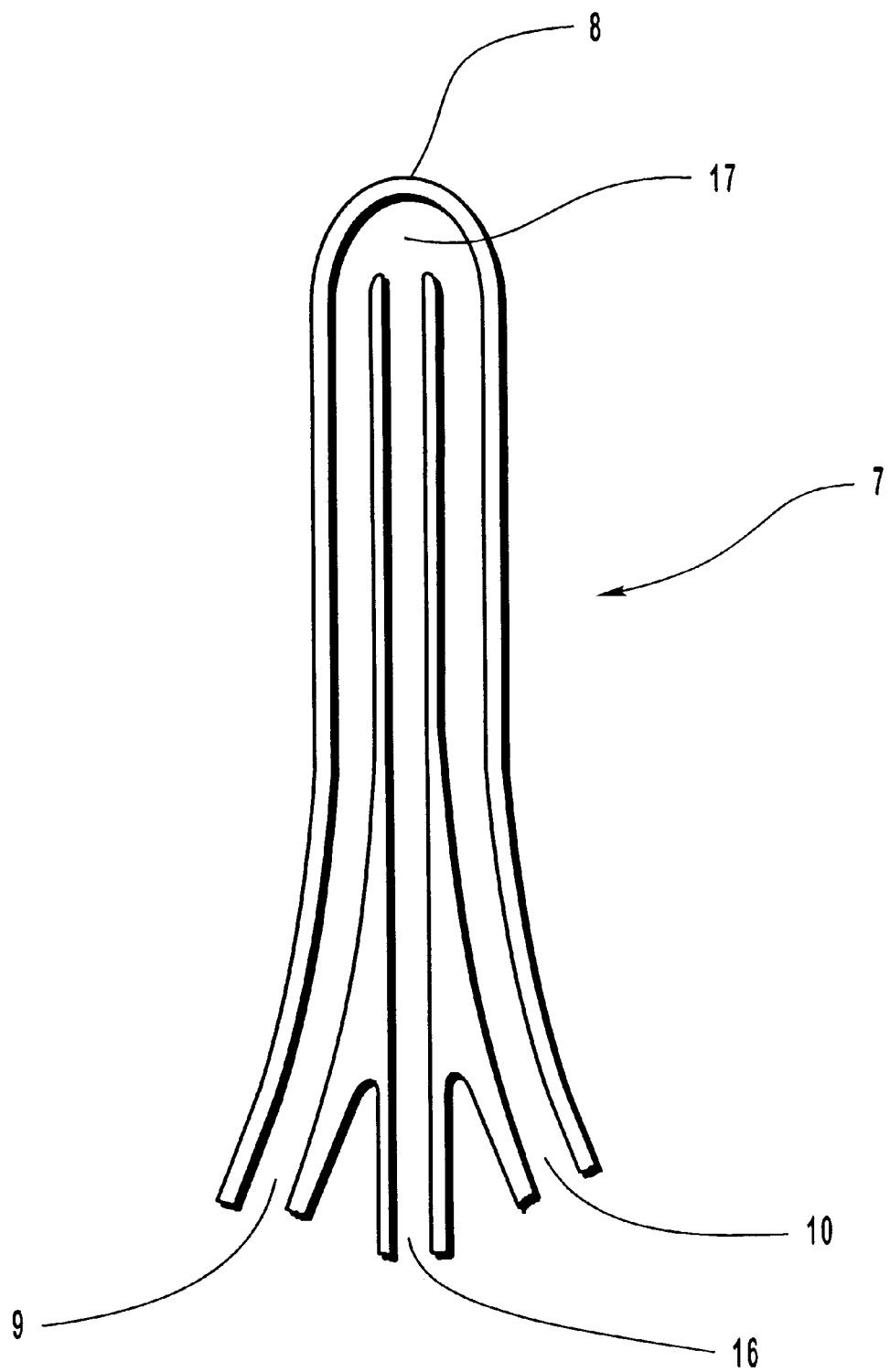
FIG. 6 is a cross-sectional view of a three-lumen catheter for mixing fluids to produce heat near the tip.

It is known that hypothermia is one of the most effective therapies available for stroke victims, head trauma victims, and others suffering similar diseases and injuries. Known methods and devices for inducing hypothermia in an animal rely on cooling methods, cooling devices or drug therapies that impair normal body temperature regulation. It is novel to propose warming to induce hypothermia. It is also known that body temperature is well-controlled in warm-blooded animals. The brain regions most important in the regulation of body temperature are in and near the hypothalamus.

It is known that small changes in hypothalamic temperature will cause physiological responses that act to restore body temperature to normal. It is novel to suggest, as is suggested in the present invention, that inducing small changes in hypothalamic temperature can be used for therapeutic effect. In addition, infusion of compounds such as melatonin also affect body temperature.

It is known that the hypothalamus 4 in humans is located near to the sphenoid sinus 3, a sinus which is accessible from the outside of a person via nasal passages 2 and the nostrils 1 and via the oral passage 5. A novel aspect of the present invention is the recognition that application of heat to the sphenoid sinus will warm the hypothalamus and cause a physiological cooling response. Warming of the sphenoid sinus will warm the hypothalamus of a person with normal blood flow but will not greatly warm other brain regions. Modelling suggests that the temperature near to a heat source in a well-perfused brain rises significantly only at the points nearest the heat source. Thus, application of heat to a nasal passage, sinus or directly to the hypothalamus will have only local direct effects on brain temperature, will not significantly raise temperature in other, more distal, brain regions, and will lead to global hypothermia.

The exact parameters of warming a nasal passage, sinus or hypothalamus, or combinations of these, may vary, as will be appreciated by those skilled in the art of medical practice, but will necessarily involve providing a warming means, applying said warming means so as to warm the hypothalamus or sinus or nasal passages, or combinations of these, to between about 38° C. and about 50° C. As said warming means is being applied, compounds may be introduced into a nasal passage or sinus. In some cases, it may be desireable as well to apply cooling measures to the animal, such as blowing air across exposed skin, applying cold dressings to exposed skin, and so forth. However, moderate cooling measures, if any, are preferred, since lowering the skin temperature will raise the hypothalamic temperature setpoint. For this reason, it may be advantageous to warm portions of the skin in order to lower the hypothalamic setpoint and so aid in maintaining a lowered body temperature.

DESCRIPTION OF APPARATUS OF THE INVENTION

Heat may be applied to a nasal passage or a sinus or to a nasal passage and a sinus through the breathing of a warm gas, such as air mixed with steam or water mist (in a ratio of approximately 0% to 40% by volume) at a temperature between about 38° C. and about 50° C., although other temperatures may also be effective. Preferred temperatures are between about 38° C. and 43° C. This gas may be supplied, for example, to a nasal passage via a hollow tube 6, of a size smaller than a human nostril. Tubes effective for this purpose are approximately 0.1" to approximately 0.5" in outer diameter, may be thin-walled or thick-walled, and may be made, for example, of Tygon tubing. This tube may be inserted a short distance (for example, less than 0.5") into a nasal passage, or may be inserted farther into a nasal passage (for example, approximately 1" or more). Care must be taken that the animal breathes sufficient oxygen for health, and that sensitive nasal tissue is not scalded. If higher temperature gases are used, or higher fractions of steam or other warm gas, then smaller diameter tubes which do not fully occlude the nostril and so allow passage of air into the nasal passage are preferred. If lower temperature gases, nearer to 38° C. than 50° C., are used, then larger diameter tubing which occludes the nostril may be used.

Similarly, heat may be applied to a sinus, preferably the sphenoid sinus, through direction of a heated gas such as air mixed with steam via a tube or catheter 7. This heated gas may be air mixed with steam (in a ratio of approximately 0% to 40% by volume) at a temperature between about 38° C. and about 50° C., although other temperatures may also be effective. Preferred temperatures are between about 38° C. and 43° C. This gas may be supplied, for example, to a sinus by a hollow tube with an outside diameter of between about 0.05" and about 0.25". This hollow tube may be thin-walled or thick-walled, and is made, for example, of about 10 cm of flexible tubing with a smooth 4 mm curve at the distal end. This tube may be inserted through a nostril or through the mouth and oral cavity to gain access to a nasal passage above the palate and then into a sinus. Insertion of this tube may be aided by a guide tube, a guide wire, or other implement. Care must be taken that sensitive tissue is not scalded or damaged during insertion. Insertion of this tube is preferably done using methods in common use for introduction of drain tubes into inflamed sinuses for the purpose of draining accumulated fluids.

A nasal passage or sinus may be also warmed by an apparatus which is itself heated and delivers heat. One such apparatus comprises a closed-ended flexible tube containing warm gases, such as the mixtures of steam and air, or other warm gases, or preferably containing a warm fluid, such as warm saline or other liquid, capable of being introduced into a nasal passage or sinus. Warm fluids are preferred over warm gases in this embodiment because their higher heat capacity and greater mass make them more effective to warm the tissue with which they are in contact. The temperature of said gas or fluid may be between about 38° F. and 50° C. Preferred temperatures are between about 38° C. and 43° C. Such an apparatus can be a tube with a single lumen and a distal end blocked to prevent outflow of hot gases or fluids. In a preferred embodiment, this apparatus comprises a tube with at least two inner lumens, at least one for inflow of warm fluid or gas 9, at least one for outflow of warm fluid or gas 10, with a distal end of said tube blocked to prevent outflow of the warm fluid or gas enclosed 8. Constant flow of said warm fluid or gas is maintained to provide continuous heating to the nasal passage or sinus. In a preferred embodiment, said closed end is a distal end comprised of thinner wall thickness than the lateral wall of the apparatus. An effective thickness for the blocked distal end is between about about 0.001" and about 0.05". In another preferred embodiment, said distal end is constructed of a thin flexible material, such as latex rubber or polyethylene of a thickness between about 0.001" and about 0.05" effective for transferring heat and capable of expanding or "ballooning out" to fill space surrounding it under application of internal positive pressure. This apparatus may be inserted through a nostril or through the mouth and oral cavity and then to a nasal passage above the palate and into a sinus. Insertion of this apparatus may be aided by a guide tube, a guide wire 11, or other implement. Care must be taken that sensitive tissue is not scalded or damaged during insertion. Insertion of this apparatus is preferably done using methods in common use for introduction of drain tubes into inflamed sinuses for the purpose of draining accumulated fluids.

Another such apparatus effective to warm a nasal passage or sinus comprises an electrical warming device 12 attached at an end of a flexible tube, rod or catheter capable of being introduced into a nasal passage or sinus. Said electrical warming device may be a thermocouple, Peltier device, electrical heating element, or the like. In a preferred embodiment the electrical warming is obtained by passing electrical current through an insulated coil of nichrome wire (30 to 36 AWG, coil outer diameter 0.04") connected to insulated copper or silver wires (26 to 30 gauge, twisted wire) insulated with a flexible insulating coating of an insulating material such as polyimide or epoxy. The heating element is preferably shaped in a helical coil with an outer dimension of about 0.08" diameter and contained inside an insulating coating. Effective temperatures at the heating element are between about 38° C. and about 50° C. Preferred temperatures are between about 38° C. and about 43° C. to provide warming of the nasal passage or sinus. In a preferred embodiment, a temperature sensor 13 is enclosed with the coil to provide temperature feedback to control the applied temperature. This apparatus may be inserted through a nostril or through the mouth and oral cavity and to a nasal passage above the palate and then into a sinus. Insertion of this apparatus may be aided by a guide tube, a guide wire, or other implement. Care must be taken that sensitive tissue is not scalded or damaged during insertion. Insertion of this apparatus is preferably done using methods in common use for introduction of drain tubes into inflamed sinuses for the purpose of draining accumulated fluids.

Heating of the hypothalamus directly may be accomplished by insertion of heated tubes or electrical devices, and other devices of similar effects, directly into the hypothalamus though surgical procedures. Preferred apparatus are not flexible tubes, but are made of medical grade stainless steel 14, of an outside diameter between about 0.01" and about 0.08". Electrical methods of heating are preferred over methods utilizing heated fluids or gases for this embodiment of the invention. Preferred electrical methods and apparatus include heating elements such as thermocouples, Peltier devices and resistive heating wires such as Nichrome wire provided at the tips of stainless steel rods. In addition, the delivery of radio-frequency current is effective to warm the hypothalamus. Electrical stimulation of neurons in the hypothalamus is also effective to stimulate hypothalamic neurons to trigger a physiological cooling response.

Heating of the hypothalamus may be effected by infrared radiation delivered to the inside of the sphenoid sinus or nasal passage by an infrared source such as a heated coil inside a thermally cooled jacket. In this embodiment, warming of the hypothalamus is effected by either infrared radiation alone, or by infrared radiation along with heat delivered to the hypothalamus by conduction through intervening tissue.

Physiological cooling responses may be initiated by introduction of chemical compounds into a nasal passage and a sinus, at the same time as warm gases or heat is introduced, or in the absence of said heating. Compounds such as melatonin, capsaicin and other compounds are effective to induce a physiological cooling response. Effective concentrations of melatonin are between about 0.1 nM and about 100 nM. Effective concentrations of capsaicin are between about 1 nM and about 1 uM.

It is to be understood that while the invention has been described in conjunction with preferred specific embodiments thereof, the foregoing description, as well as the examples which follow, are intended to illustrate and not limit the scope of the invention. Other aspects, advantages and modifications within the scope of the invention will be apparent to those skilled in the art to which the invention pertains.

EXAMPLE 1

This example illustrates the use of warm gas to warm a nasal passage, sinus and hypothalamus. A mixture of 25% steam and 75% air (v/v) is combined in a chamber to which are connected two flexible Tygon tubes of outer diameter 0.125" which are inserted into the nostrils of a human subject. The human subject breathes the warm gas mixture normally through the nose. In approximately 5 minutes, the subject begins to sweat. This physiological cooling response is effective to lower the animal's body temperature.

EXAMPLE 2

This example illustrates the use of a warming tube inserted into the sphenoid sinus via a nostril. The warming tube is a flexible tube with two lumens. Warm saline (43° C.) at a pressure head of 50 cm flows towards the distal end of the warming tube in one lumen, and returns via the other lumen at a pressure head of 0 cm. The distal end of the warming tube opens into and is enclosed by a distensible balloon made of latex rubber (wall thickness 0.005") which acts to direct the warm fluid flow from the inflow tube to the outflow tube. A stainless steel guide wire 11 cm in length with a shapeable tip, gently curved for the last 4 mm, is inserted into the guidewire lumen and is used to direct the distal end of the warming tube into the sphenoid sinus. The latex rubber balloon at the distal end of the warming tube expands into the sphenoid sinus once the outflow pressure head becomes positive following partial occlusion of the outflow. The circulation of warm saline inside the balloon warms the sphenoid sinus, the skull and the brain structures adjacent the sphenoid sinus, including the hypothalamus, and the animal begins to sweat. This physiological cooling response is effective to lower the animal's body temperature.

EXAMPLE 3

This example illustrates the use of warm gas to warm a nasal passage, sinus and hypothalamus and the additional use of compounds effective to increase the hypothermia induced by warming a nasal passage, sinus and hypothalamus. A mixture of 25% steam and 75% air (v/v) with added melatonin and capsaicin is combined in a chamber to which is connected a two-lumen flexible polyethylene extrusion of outer diameter 4 mm which is inserted into the nostrils of a human subject. The melatonin and capsaisin are added to the mixing chamber via an atomizer spray as a solution in saline (0.9% sodium chloride) of 10 nM melatonin, 1 mg/mL bovine serum albumin and 100 nM capsaicin. The human subject breathes the warm gas mixture normally through the nose. In approximately 5 minutes, the animal begins to sweat. This physiological cooling response is effective to lower the animal's body temperature.

EXAMPLE 4

This example illustrates the use of direct heating in the hypothalamus to produce a physiological cooling response. Standard imaging techniques are used to image the brain of the human patient prior to any surgical procedures. Accepted neurosurgical procedures are followed when exposing the skull and drilling a small hole in the skull 15, inserting a guide-tube under sterotactic control. After local anesthetic is applied, a Leksell stereotactic frame is applied to the head of a human patient and an incision in the scalp is made, exposing the skull. A single 3-mm twist drill hole is made in the exposed skull anterior to the coronal suture approximately 2 cm from the midline. The dura is penetrated with a sharp probe and a 1.1 mm guide tube is stereotactically placed in the cerebrum so that the tip is within 1 cm of the anterior hypothalamus. A sterile microelectrode is attached to a hydraulic microdrive and the tip of the electrode is advanced down the guide tube until it protrudes from the guide tube into the pre-optic/anterior hypothalamic region of the hypothalamus. Monopolar radio-frequency stimulation is imposed. The ground is 3.5 inch, 18-gauge needle placed into a deltoid muscle. Measurement of the temperature of the electrode tip is used to control the power such that the temperature rise at the electrode tip is limited to 1° C. The patient begins sweating and vasodilation begins within 5 minutes, and the patient's body temperature begins to drop.

EXAMPLE 5

This example illustrates the use of a chemical warming device to produce a physiological cooling response in a human. patient This chemical warming device comprises a guide wire, fluid reservoirs and pumps, and a flexible polyethylene tube of outer diameter 0.1" with three lumens: two of 0.03" inner diameter, one of 0.015" inner diameter 16. The distal end of this tube is occluded with all three lumens opening into a common mixing chamber 17 of 0.08" diameter and 0.04" breadth. Distilled water flows in both of the larger diameter lumens, one lumen serving for inflow of distilled water, the other for outflow. The third, smallest lumen contains an aqueous mixture of 100 mM KOH. Liquid in all three tubes is maintained at a pressure less than ambient pressure to insure that, in the event of failure, no liquid will escape into the patient. Liquid flow is maintained by a siphon effect, with the two inflow reservoirs and one outflow reservoir being situated below the level of the patient's head. KOH solution is introduced into the mixing chamber by increasing the flow rate of that liquid (with a concomitant increase in outflow rate). This causes the KOH solution to mix with and to be diluted in the distilled water, thereby releasing heat in the region where mixing occurs. The chemical warming device is used in the following manner: the distal end of the chemical warming device is directed near to the sphenoid sinus as distilled water is flowing through the tube; when the tube is positioned as desired, KOH solution flow is initiated, with an increase in the fluid outflow rate as well to insure adequate and appropriate removal of fluid from the mixing chamber situated in the distal end of the tube, thereby heating the tip region of the chemical warming device, warming a sinus, and inducing a physiological cooling response.

I claim:

1. A method for inducing hypothermia in an animal with skin and a hypothalamus, wherein said animal is in need of therapeutic cooling, said method comprising directing heat to said hypothalamus, and warming a portion of the skin of said animal, to cause said animal to respond with a physiological cooling response to induce hypothermia in said animal.

2. The method of claim 1 wherein the step of directing heat comprises applying heat within said hypothalamus.

3. The method of claim 1, further comprising the step of cooling said animal.

4. The method of claim 3, wherein said cooling is done using cold coverings, moving air, cold fluids, intravenously injected cold fluids, muscle relaxants, drug treatments, breathing cold gases, wetting skin, wetting hair, cold support or peritoneal lavage.

5. A method for inducing hypothermia in an animal with skin, an oral passage, a nasal passage, a sinus, and a hypothalamus, wherein said animal is in need of therapeutic cooling, said method comprising directing heat to said hypothalamus via the nasal or oral passage to the sinus, and warming the skin of said animal, to cause said animal to respond with a physiological cooling response to induce hypothermia in said animal.

6. The method of claim 5, wherein the sinus is a sphenoid sinus.

7. The method of claim 5, further comprising the step of cooling said animal.

8. The method of claim 7, wherein said cooling is done using cold coverings, moving air, cold fluids, intravenously injected cold fluids, muscle relaxants, drug treatments, breathing cold gases, wetting skin, wetting hair, cold support or peritoneal lavage.

9. A method for inducing hypothermia in an animal with skin and a hypothalamus, said method comprising warming a portion of the skin of said animal, and electrically stimulating said hypothalamus, to cause said animal to respond to said electrical stimulation with a physiological cooling response to induce hypothermia in said animal.

10. The method of claim 9, further comprising the step of cooling said animal.

11. The method of claim 9, wherein said cooling is done using cold coverings, moving air, cold fluids, intravenously injected cold fluids, muscle relaxants, drug treatments, breathing cold gases, wetting skin, wetting hair, cold support or peritoneal lavage.

* * * * *